US010646710B2

(12) United States Patent
Feinstein

(10) Patent No.: US 10,646,710 B2
(45) Date of Patent: May 12, 2020

(54) MEDICAL WOUND COVERING EMPLOYING ELECTRICAL STIMULATION TO CONTROL BLOOD FLOW

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 15/996,141

(22) Filed: Jun. 1, 2018

(65) Prior Publication Data

US 2019/0366083 A1   Dec. 5, 2019

(51) Int. Cl.
*A61N 1/32* (2006.01)
*A61N 1/02* (2006.01)
(Continued)

(52) U.S. Cl.
CPC .............. *A61N 1/323* (2013.01); *A61B 46/20* (2016.02); *A61N 1/025* (2013.01);
(Continued)

(58) Field of Classification Search
CPC .............. A61N 1/0492; A61N 1/36014; A61N 1/0468; A61N 1/0476; A61N 1/04;
(Continued)

(56) References Cited

U.S. PATENT DOCUMENTS 5,817,138 A   10/1998   Suzuki
5,974,342 A   10/1999   Petrofsky
(Continued)

FOREIGN PATENT DOCUMENTS

EP         0830875 A2    3/1998
KR     20090011617 U    11/2009
(Continued)

OTHER PUBLICATIONS

Hee-Kyung Jin, et al, "Effect of Electrical Stimulation on Blood Flow Velocity and Vessel Size", published online Mar. 6, 2017, https://www.ncbi.nlm.nih.gov/pmc/articles/PMC5385976/.
(Continued)

*Primary Examiner* — Deborah L Malamud
(74) *Attorney, Agent, or Firm* — Forge IP, PLLC

(57) ABSTRACT

A medical wound covering for controlling blood flow includes a flexible sheet for covering or surrounding the anatomical site of a wound, such as a surgical drape. The flexible sheet includes a plurality of electrodes electrically connectible to a stimulation power supply. Upon receipt of power from the stimulation power supply, the electrodes supply electrical impulses to the anatomical site of the wound in order to stem or arrest undesired bleeding. In some cases, the stimulation power supply is an interferential therapy power supply, and a pair of electrodes supplies electrical impulses at two different frequencies, the electrical impulses provided at two different frequencies giving rise to at least one beat impulse having an interference frequency. The beat impulse activates the sympathetic nerves to induce vasoconstriction in the local blood vessels. Alternatively, the beat impulse can be programmed to target the parasympathetic nerves if vasodilatation is desired.

24 Claims, 9 Drawing Sheets

(51) Int. Cl.
*A61B 46/20* (2016.01)
*A61N 1/36* (2006.01)

(52) U.S. Cl.
CPC ......... *A61B 2046/205* (2016.02); *A61N 1/326* (2013.01); *A61N 1/36014* (2013.01)

(58) Field of Classification Search
CPC ........ A61N 1/0424; A61N 1/205; A61N 1/32; A61N 1/36; A61N 1/0484; A61N 1/18; A61N 1/00; A61N 1/02; A61N 1/0472; A61N 1/08; A61N 1/326; A61B 5/4836; A61B 5/6804; A61B 5/6805; A61B 5/681; A61H 2201/1645; A61H 2201/165
See application file for complete search history.

(56) References Cited

U.S. PATENT DOCUMENTS

| | | | |
|---|---|---|---|
| 6,826,429 | B2 | 11/2004 | Johnson et al. |
| 7,647,114 | B2 | 1/2010 | Libbus |
| 9,956,405 | B2 | 5/2018 | Goldwasser et al. |
| 2010/0268300 | A1 | 10/2010 | Ramos Leal et al. |
| 2013/0041235 | A1* | 2/2013 | Rogers ................ A61B 5/6867 600/306 |
| 2014/0194949 | A1 | 7/2014 | Wichner |

FOREIGN PATENT DOCUMENTS

| | | |
|---|---|---|
| KR | 20140143938 A | 12/2014 |
| WO | WO2018046570 | 3/2018 |

OTHER PUBLICATIONS

Francisco V. Santos, et al, "Interferential electrical stimulation improves peripheral vasodilatation in healthy individuals", Brazilian Journal of Physical Therapy, vol. 17 No. 3 São Carlos May/Jun. 2013; http://dx.doi.org/10.1590/S1413-35552012005000092.

Akram Shahrokhi, et al, "Impact of interferential current on recovery of pressure ulcers grade 1 and 2", Iranian Journal of Nursing and Midwifery Research, Feb. 2014; 19(7 Suppl1): S91-S96, https://www.ncbi.nlm.nih.gov/pmc/articles/PMC4402989/.

* cited by examiner

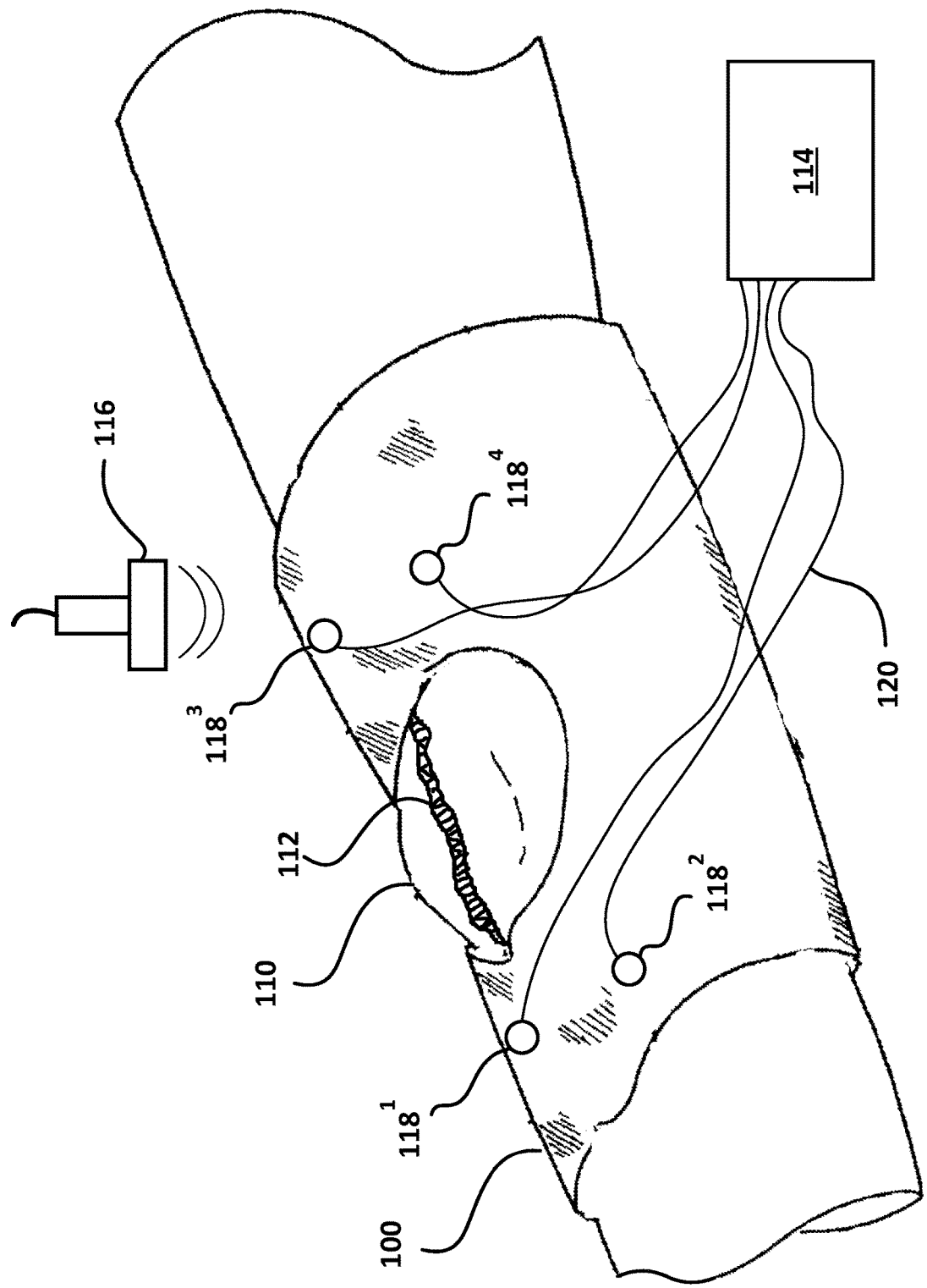

MEDICAL WOUND COVERING EMPLOYING ELECTRICAL STIMULATION TO CONTROL BLOOD FLOW

FIELD OF THE INVENTION

The invention relates to system employing the use of an electrical stimulator, such as an Interferential Current (IFC) device, or other type of deep penetration electrical stimulation that is non-invasive and external (i.e., transcutaneous), for controlling blood flow. More specifically, the invention relates to a medical covering, such as a surgical drape or other wound dressing incorporating a mechanism for the delivery of electrical stimulation to the sympathetic/parasympathetic nerves of the relevant anatomy to slow or stop bleeding or to increase blood flow, depending on the medical need.

BACKGROUND OF THE INVENTION

There exist various types of medical environments in which it is desirable to dress a wound, typically with a fabric, paper, plastic, or similarly flexible and/or stretchable material. This is done for several reasons, including protecting the wound from infection, absorbing fluids exuded from the wound, facilitating healing, and/or stemming bleeding.

One such scenario is the use of surgical drapes in an operating room. In a typical operating room, a patient is positioned on an operating table for one more medical practitioners to perform a surgical procedure. At the beginning of the procedure, it is usually desirable to create a sterile field around the surgical site to reduce the possibility of infection of the patient. Generally, a sterile field is created by draping a sterile material over the patient in such a manner as to leave an opening only at the actual site of an incision. In some cases, an adhesive drape, such as a Steri-Drape™, is secured to the surgical site of the patient. In some cases, the incision is made directly through the sterile adhesive drape, such as in a Coban™.

Bleeding is an unavoidable and ever-present consideration in any medical condition or intervention that involves a skin incision (or skin laceration) or procedure directed to deeper/internal organ structures. It is particularly important when performing surgery. This can be especially critical in those cases where the procedure or medical situation has potential to lead to unexpected hemorrhaging. Bleeding, whether minor or major, always presents several challenges.

Undesirable flow of blood in the operative site or operative field must be managed to preserve unobstructed view of anatomic structures to be incised or repaired to avoid surgical errors. This typically necessitates the involvement of an assistant, who will sponge or suction the blood as it accumulates and obscures the local anatomy. This requires an additional set of hands in the operative site, which both results in crowding of the area in which the surgeon needs to work and increases the risk of infection and accidental injury. Additionally, some medical practitioners have used drapes that contain a pouch to collect the blood (as well as other fluids). For example, during abdominal surgery, a fluid collection pouch may be placed adjacent one side of the surgical site and extending down the side of the patient, while in arthroscopy surgery, the patient's leg may be placed through a collection pouch mounted to a drape, with one sheet of the collection pouch in front of the surgical site on the limb and another sheet of the collection pouch in back of the surgical site, such that the fluid collection pouch is supported in part by the limb itself and in part by the surgical drape (to which the fluid collection pouch is attached). Some drapes include fluid collection pouches with a port for connecting a suction hose to help facilitate removal of the fluid. However, collection pouches pose numerous difficulties, including that the positioning of the pouch can make it difficult to adequately expose the surgical site, that it may not provide an optimal opening for capturing the blood, and that it may leak.

More importantly, intraoperative attempts to stem or stop the blood flow, and the need to arrest post-operative bleeding, have traditionally required the use of additional instruments and/or agents. In particular, pneumatic tourniquets are often employed for this purpose. This consists of using an inflatable cuff to provide tissue compression to occlude the blood flow. The use of such devices suffers from a number of disadvantages.

The use of a tourniquet to stop intraoperative bleeding is not always effective. Often, bleeding will still occur due to an under-pressurized cuff, insufficient exsanguination, improper cuff selection, a loosely applied cuff, calcified blood vessels resistant to the cuff, or insufficiently quick inflation/deflation.

Additionally, the use of a tourniquet to control bleeding at the surgical site has been shown to increase morbidity. A common problem is nerve injury, which appears to be attributable to both mechanical compression and neural ischemia, and which can result in mild transient loss of function to irreversible damage and paralysis. Other potential complications from the use of tourniquet are compartment syndrome, pressure sores, chemical burns, digital necrosis, deep venous thrombosis leading to pulmonary or venous embolization, pain, thermal damage to tissues, and rhabdomyolysis. A common post-operative complication from use of a tourniquet is hematoma or hemarthrosis formation, from the tourniquet pressure during surgery being too low and allowing arterial blood pressure to push blood from the arterial system past the tourniquet into the extremity while the tourniquet provides enough pressure to prevent the venous blood flow system from returning the blood The venous blood ends up pooling in the operative site compromising the surgical field of view, or in the surrounding tissues resulting in a postoperative hematoma, with its many associated complications and difficulties. Similarly, when the tourniquet is deflated at the conclusion of the procedure there is an immediate post-operative reactive hyperemia or vasodilatation, which predisposes one to bleeding in the operative site after the wound is closed.

Further, bleeding is more severe and harder to control in cases where a tourniquet is not (or cannot) be utilized. For example, when performing arthroscopic or open surgery in the shoulder, the physical location of the shoulder relative to the rest of the body and the arteries through which blood flows to the shoulder makes it impractical to use a tourniquet to control bleeding. As a result, there is typically significant bleeding during shoulder surgery. For example, in order to control this bleeding at the surgical site during an arthroscopic procedure, it is necessary to withdraw the surgical instrument and insert an electrocautery probe through the same opening. To utilize electrocautery, the body of the patient is grounded, and the tip of the energized electrocautery probe is pressed against the tissue from which the blood is flowing. A high frequency electrical current flows from the probe through the tissue of the patient, and the tissue, including any open blood vessels therein, is heated by the current, coagulating the tissue and sealing the open ends of the blood vessels. The blood produced prior to this must then be removed from the surgical site using a flow of sterile fluid (irrigation) to restore visibility in the surgical site, and then the surgical tool is reinserted to resume the surgery.

This removal of the surgical instrument when bleeding occurs, the subsequent insertion of the electrocautery probe, the removal of the probe after cauterization, and the reinsertion of the surgical instrument thereafter is a difficult, time-consuming task that only further increases risk of injury or infection. Moreover, during the time between the removal of the surgical instrument and the insertion of the electrocautery probe, a significant amount of blood can accumulate at the surgical site, making it difficult to visually locate the actual source of the bleeding. Even if one were able to use a single surgical instrument that was also able to act as an electrocautery probe, the cauterization process inflicts undesirable trauma to the relevant tissue.

Efforts to control bleeding often also include the use of pharmaceutical agents. For example, In the past, it was customary to take a unit of the patient's own blood three weeks before the surgery (to allow the body to replenish), which would then be an extra unit of blood to be used during the surgical and post-operative periods, as a method to avoid the complications of HIV and Hepatitis from regular typed and crossed transfusions from the general blood bank. However, this approach still had problems, as it often resulted in a lower starting blood count (patients didn't regenerate to normal levels before the surgery in a three week time frame). It also did nothing to control the actual problem of bleeding. Currently, transfusions, and the complications associated with them, are more rare because of the use of tranexamic acid, which is sometimes administered (both before and after surgery) to slow the breakdown of blood clots, and thereby prevent blood loss, thus reducing the need for blood transfusions. Additionally, pharmacological agents such as bupivacaine and other local anesthetics are sometimes administered preoperatively (as in nerve blocks for regional anesthesia) or to treat post-operative and recovery pain. To help extend the time that these agents are effective, they are often combined with epinephrine. Epinephrine causes vasoconstriction so that the body takes longer to remove the local anesthetic from the area being treated. However, epinephrine has multiple other actions, such as causing tachycardia or elevated blood pressure, that are detrimental to recovery and can cause serious intraoperative and postoperative complications. Such use of epinephrine in this manner needs to be monitored (vital signs) to be sure complications are not occurring. Because these agents or combinations of them can have undesirable side effects, it is preferable to employ a method of controlling intraoperative and post-operative bleeding that does not rely on them.

Therefore, what is desired is a system and method for controlling blood flow at a surgical site or other wound that does not require having to clear and remove large, or small but strategically localized, amounts of blood exuded by the wound. What is further desired is a system and method for preventing blood loss that does not require the use of additional devices that cause other trauma to the body. What is also desired is a system and method for preventing blood loss that does not depend upon the administration of pharmaceuticals.

SUMMARY OF THE INVENTION

Accordingly, one object of the present invention to provide a system that is able to stop (or at least slow), the bleeding from a wound resulting from surgery or injury, thereby eliminating (or at least mitigating) the need to manage excessive fluid flow.

It is another object of the present invention to provide such a system for slowing or stopping bleeding that does not require the use of a tourniquet or electrocautery device.

It is yet another object of the present invention to provide such a system that does not require pharmacological effects in order to slow or stop the bleeding.

It is still another object of the invention to provide a system that, if needed, stimulates blood flow and vasodilatation if that is a condition deemed to be needed for the particular procedure being undertaken, such as treating endovascular arterial sclerotic blockage with an endovascular plaque-eating or clearing instrument.

In order to overcome the deficiencies of the prior art and to achieve at least some of the objects and advantages listed, one exemplary embodiment of the invention comprises a medical wound covering for controlling blood flow, including a flexible sheet for covering the anatomical site of a wound, where the flexible sheet includes a plurality of electrodes electrically connectible to a stimulation power supply, and where the electrodes supply electrical impulses to the anatomical site of the wound when receiving power from the stimulation power supply.

In some advantageous embodiments, the flexible sheet is a surgical drape, which in some cases, is an adhesive drape. In other embodiments, the medical wound covering is a medical dressing, while in other embodiments, it is a bandage.

In some embodiments, the flexible sheet is configured to have a shape corresponding to shape of a foot. In other embodiments, a neoprene brace is employed.

In certain advantageous embodiments, the stimulation power supply is an interferential therapy power supply, and the plurality of electrodes includes at least one pair of electrodes supplying electrical impulses at two different frequencies, the electrical impulses provided at two different frequencies giving rise to at least one beat impulse having an interference frequency. In some of these embodiments, the at least one beat impulse has a sympathetic nerve stimulation property to induce vasoconstriction of blood vessels. In some cases, the flexible sheet includes a plurality of pairs or electrodes, each pair giving rise to at least one beat impulse having an interference frequency.

In some embodiments, the electrodes are embedded within the sheet. In other embodiments, each electrode includes an adhesive on a surface thereof, with which the electrode is affixed to an outer surface of the sheet. In still other embodiments, the sheet includes a plurality of enclosed chambers, each of the chambers having an electrically conductive liquid therein, the electrodes comprising the electrically conductive liquid. In yet other embodiments, the sheet includes a plurality of electrically conductive fabric segments of fabric, the electrodes comprising the electrically conductive fabric segments.

In certain embodiments, the invention further includes a controller, a stimulation power supply in communication with the controller, and a sensor providing sensor feedback to the controller, the sensor indicative of the state of blood flow at the anatomical site of the wound, and the controller causes the stimulation power supply to supply power to the plurality of electrodes based at least in part on the state of blood flow. In some of these embodiments, the sensor is a Doppler ultrasound probe.

In some embodiments, each electrode includes an electrical connector for connecting a wire to the stimulation power supply. In other embodiments, the stimulation power supply communicates wirelessly with the electrodes.

The invention also comprises a medical wound covering for controlling blood flow, including an interferential therapy power supply, and a surgical drape for covering the anatomical site of a wound, the surgical drape including at least one pair of electrodes connected to the interferential therapy power supply, where the pair of electrodes supplies electrical impulses at two different frequencies when receiving power from the interferential therapy power supply, the electrical impulses provided at two different frequencies giving rise to at least one beat impulse having an interference frequency.

The invention also comprises a method of controlling blood flow with a medical wound covering, the method including covering an anatomical site of a wound with a flexible sheet having a plurality of electrodes, connecting the plurality of electrodes to a stimulation power supply, and supplying electrical impulses to the anatomical site of the wound by supplying power to the electrodes from the stimulation power supply.

In some of these embodiments, the stimulation power supply comprises an interferential therapy power supply, and the step of supplying electrical impulses to the anatomical site of the wound comprises supplying electrical impulses at two different frequencies, the electrical impulses provided at two different frequencies giving rise to at least one beat impulse having an interference frequency.

BRIEF DESCRIPTION OF THE DRAWINGS

FIG. 4A is a partially perspective view of a wound covering illustrated in FIGS. 3A-D being used on a patient in a knee surgery procedure.

DETAILED DESCRIPTION OF THE INVENTION

As used herein, the terms "electrode" and electrodes" encompass electrical coils, electrical plates, electrical conductors, conductive fabrics and gels, and any other conductive materials and devices.

Figure 1:
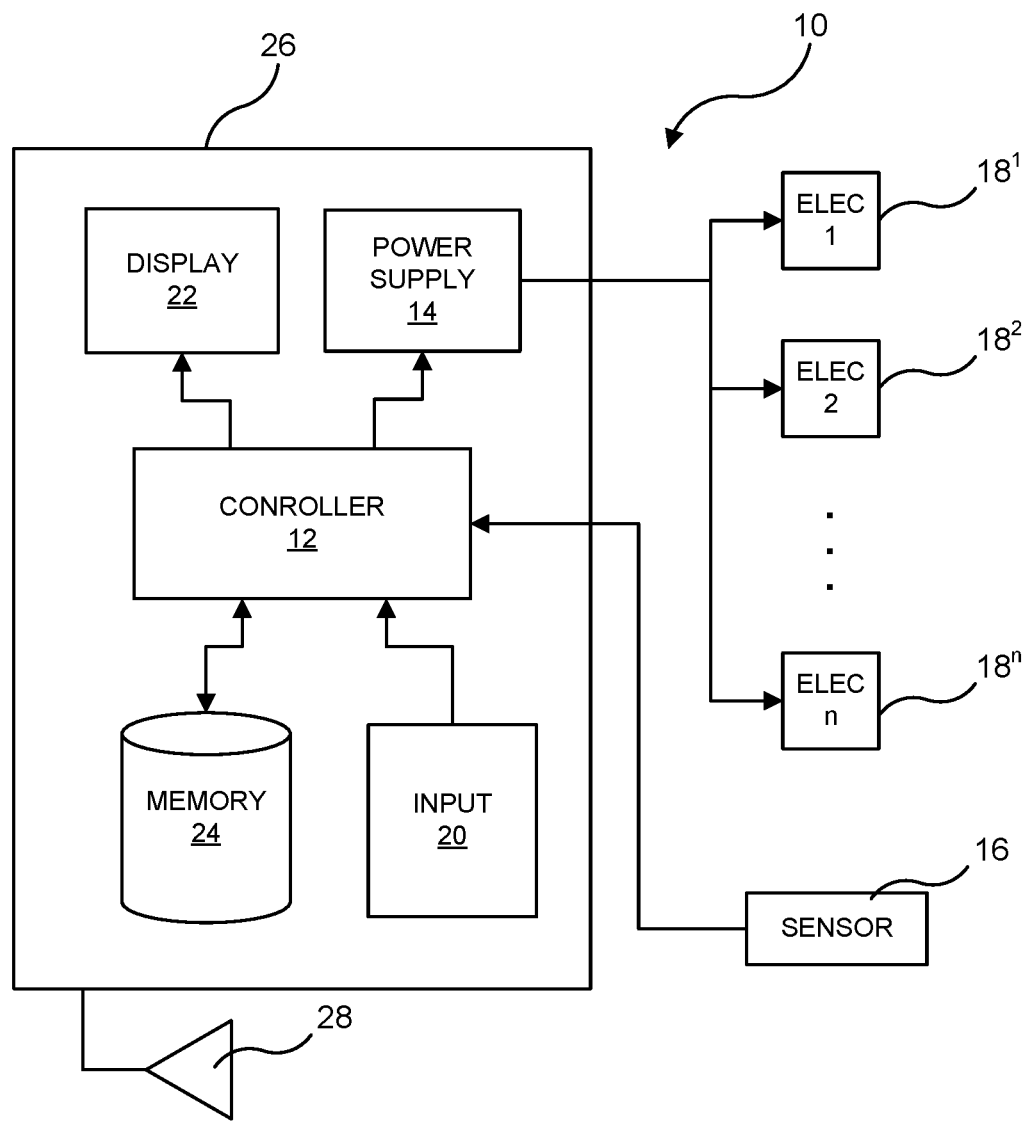
FIG. 1 is a block diagram illustrating a system for controlling blood flow with a medical wound covering in accordance with an exemplary embodiment of the present invention.

Referring to the figures in detail and first to FIG. 1, there is shown an exemplary embodiment of a system (10) for controlling blood flow in a surgery patient or other individual with a wound requiring the active control and prevention of blood loss therefrom. The system (10) includes a controller (12) and a stimulation power supply (14) in communication with the controller (12).

The system (10) also includes a plurality of electrodes ($18^1, 18^2 \ldots 18''$) in electrical communication with the stimulation power supply (14). The plurality of electrodes ($18^1, 18^2 \ldots 18''$), the location of which are described further below, are arranged to supply electrical impulses that cause activation of sympathetic and/or parasympathetic nerves when supplied power by the stimulation power supply.

The controller (12) causes the stimulation power supply (14) to supply power to the plurality of electrodes ($18^1, 18^2 \ldots 18''$) in response to a command from the controller (12) when the stemming or arresting of bleeding is required. As is explained in more detail below, the power supplied to the plurality of electrodes ($18^1, 18^2 \ldots 18''$) is such that transcutaneous electrical impulses are created in order to cause sympathetic and/or parasympathetic nerve activation.

The system (10) also includes an input mechanism (20), such as a graphical user interface, microphone for receiving voice commands, keyboard, joystick, or the like, which allows the user to enter control parameters and the like. As examples, input mechanism (20) may include a button or other type of controller to turn the device on or off manually, or to trigger activation of sympathetic and/or parasympathetic nerves.

In some embodiments, the system also includes a sensor (16) providing sensor feedback to the controller (12), and the controller (12) causes the stimulation power supply (14) to supply power to the plurality of electrodes ($18^1, 18^2 \ldots 18''$) based, at least in part, on the sensor feedback received from the sensor (16). For instance, the sensor feedback may be indicative of the blood flow rate through a relevant circulatory path of the patient, such that a medical practitioner can monitor blood flow as the electrical stimulus is being applied. The sensor (16) may comprise, for example, an ultrasound probe. In this sense, a Doppler ultrasound can be used to generate an image of the movement of blood and its velocity relative to the probe in the target area. This may be particularly desirable, for example, when direct visualization of subdermal/internal bleeding is impractical, or when the system is employing the use of a post-operative bandage and there is no person visually observing whether there is any post-operative bleeding in the wound for an extended period.

In some embodiments, the system (10) also includes a display (22) to provide visual and/or auditory output to a user of the system (10). The display (22) may also present the user with other helpful information, such as previously loaded data for the patient, or current blood flow and previously recorded blood flow rates for the targeted circulatory pathways prior to the supply of power to the electrodes ($18^1, 18^2 \ldots 18''$) such that a medical practitioner can perform a comparison to determine whether the electrical stimulus is actively affecting the targeted pathway.

The system (10) further includes a memory (24), which allows the system to store various parameters that may be employed by the controller (12), or data recorded prior to and/or during the supply of power to the electrodes ($18^1, 18^2 \ldots 18''$).

In some embodiments the system further includes the ability to transmit information and data obtained through the Internet or other mechanism to remote or off site locations for consultation or expert input, interpretation, and monitoring of data garnered during or after the procedure, or for incorporation into EMRs, or for telehealth applications.

The controller (12), stimulation power supply (14), input mechanism (20), display (22), memory (24) and an optional antenna (28) for wireless communication may be (but are not necessarily) contained in a housing (26), as should be apparent to those skilled in the art. Various types of connectors may be provided on the housing to allow for connection of the electrodes ($18^1, 18^2 \ldots 18^n$), the sensor (16), or various other devices (e.g., mobile phones, tablets, smart watches, etc.), as should also be apparent to those skilled in the art. This connection may be wired (which requires grounding in a manner similar to that of an electrocoagulation device), or wireless, as further described below.

While specific targeting for the IFC impulses will typically not be required for the present inventions, the controller (12) can be connected to a targeting device, if desired. Depending on whether the surgeon, nurse, or other medical practitioner is able to eyeball the appropriate positioning of the wound covering, or whether a more precise correlation with other surgical instrumentation (such as robotic surgery) or post-operative positioning is required, a targeting system may be employed.

For example, many imaging modalities are known that would be appropriate to collect imaging sensor data (110), including ultrasound (including Level II ultrasound, 3D ultrasound, 4D ultrasound, etc.), x-rays, computed tomography (CT) scanning, magnetic resonance imaging MRI scanning (3D or otherwise), positron emission tomography (PET), radiography, elastography, thermography, bone scanning, etc. More advanced imaging techniques involving combinations of various modalities may also be used, such as MRI-TRUS (magnetic resonance aging/transrectal ultrasound) fusion, which has been used to perform targeted prostate biopsies.

The imaging modalities used may be static, or dynamic. In addition, various functional modalities may be employed, such as Doppler ultrasound to evaluate blood flow or other forms of plethsmethography (which is measurement of blood flow dynamics) or various functional neuroimaging techniques to evaluate brain activity. Image intensification is another diagnostic modality that can be used, which affords x-ray assessment in real time with motion as in some of the ultrasound options. This can be important during procedures such as cardiac catheterizations.

Additionally, various other types of electrical sensor data may be used to assist with targeting of the IFC currents. For example, electroencephalography (EEG) may be employed for applications involving the brain, while echocardiography (EKG) may be employed for applications involving the heart. Nerve conduction tests and electromyograms (NCT and NCV) and somatosensory evoked potentials (SSEP) may also be employed.

The sensor(s) may be integrated with a robotics device, machine, or algorithm. Examples of this would be surgical robotics machines made by MAKO Surgical, Intuitive Surgical, and Restoration Robotics which respectively are used for surgically-assisted operations in terms of joint replacements, robotic abdominal surgery, robotic placement of hair transplant follicles, and robotic assisted prostate surgery. Rather than using robotics to aid surgeons, the robotics technology can be combined with IFC to give extremely accurate microscopic and larger field targeting through the IFC.

In fact, the robotics could be combined with IFC such that an individual could do essentially "IFC robotic surgery" in which the robotic assisted mechanism not only targets the area through robotic anatomic analysis, but also then the robotic arms controlled by the surgeon would place the appropriate interferential electrodes on the skin and, through the connecting robotic arm also supply the appropriate electric current with feedback through the robotic surgery targeting technology and device.

Although the use of various types of deep penetration electrical stimulation that are non-invasive and external (i.e. transcutaneous) is contemplated, the presently discussed exemplary embodiment employs interferential current (IFC) technology.

In general, IFC therapy utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current were at 4000 Hz and the other current at 3900 Hz, the resultant beat frequency would be at 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current.

In other words, the lower the stimulation frequency, the greater the resistance to the passage of the current, so more discomfort is experienced. The skin impedance at 50 Hz is approximately 3200 ohms, whilst at 4000 Hz, it is reduced to approximately 40 ohms. The result of applying this latter frequency is that it will pass more easily through the skin and any other tissues before hitting the target tissue or organ with a therapeutic beat frequency resulting in the desired physiologic response from the target organ or tissue, requiring less electrical energy input to the deeper tissues, giving rise to less discomfort.

Figure 2:
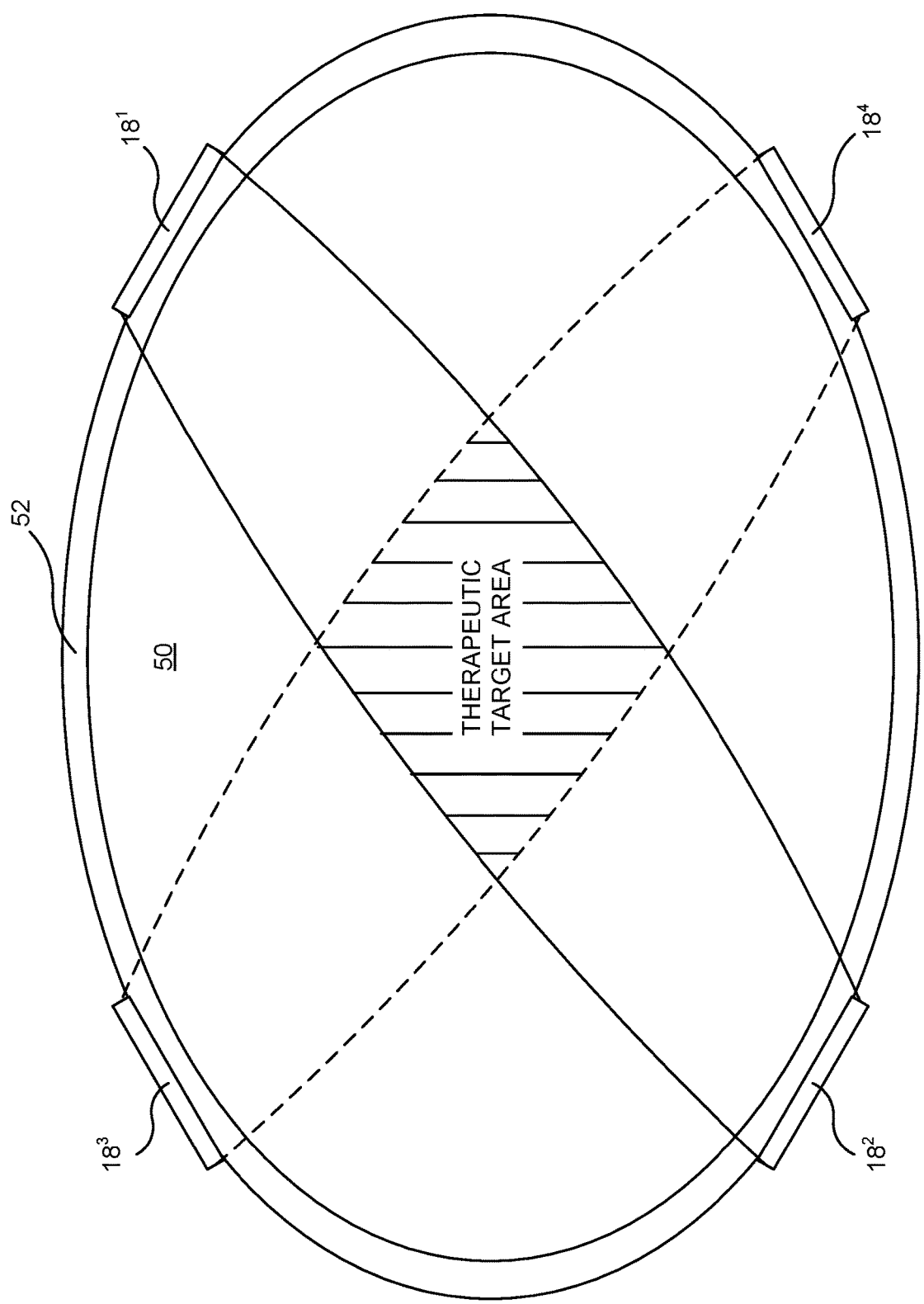
FIG. 2 is schematic view illustrating operational characteristics of the system shown in FIG. 1.

Referring now to FIG. 2, an exemplary arrangement of electrodes employing IFC therapy is shown applied to the epidermis (52) of a patient (50) at the site of a wound. In this example, a first pair of electrodes ($18^1, 18^2$) supplies transcutaneous electrical impulses at a first frequency (represented by solid lines) and a second pair of electrodes ($18^3, 18^4$) supplies transcutaneous electrical impulses at a second frequency (represented by dashed lines) different than the first frequency. The transcutaneous electrical impulses provided at the first and second frequencies giving rise to a beat impulse in a Therapeutic Target Area (located at the position shown in FIG. 2 where the area defined by solid lines and the area defined by dashed lines overlap) having an interference frequency. The beat impulse results in activation of the sympathetic and/or parasympathetic nerves.

The beat impulse is controlled depending on the type of nerve/tissue/organ to be stimulated, as well as on real-time feedback of the elicited response (as explained in more detail below). For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

As has been recognized, nerves will sometimes accommodate to a constant signal. Accordingly, in some embodiments, the electrodes vary the beat frequency, either automatically or upon user input from a medical practitioner, to produce a frequency "sweep" that avoids this problem.

Figure 3A:
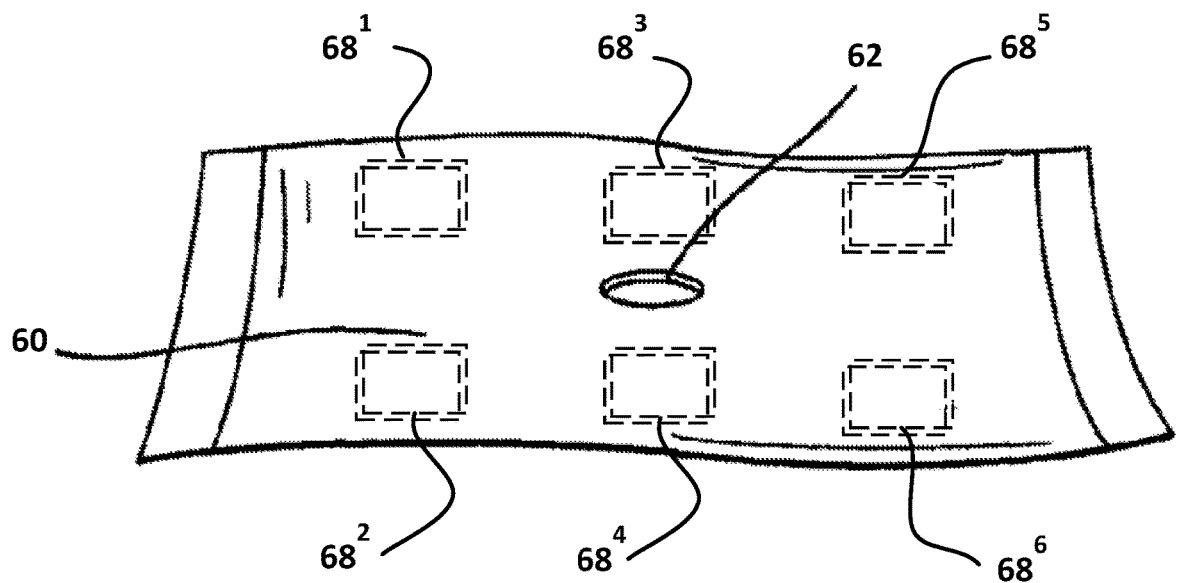
FIGS. 3A-D are perspective views of exemplary wound coverings used in the system illustrated in FIG. 1.

Referring now to FIG. 3A, an exemplary medical wound covering is shown. The covering comprises a sheet (60), which, in this particular embodiment, is a surgical drape. The drape (60) may be a typical shape, such as rectangular, square, oval, or the like, or may be particularly shaped to suit the particular type of surgical procedure and part of the anatomy being treated. In some cases, the drape (60) is adhesive in order to better maintain sterility at the site of the surgical incision, but in some embodiments the drape (60) is a standard non-adhesive drape. The drape (60) may be made of polypropylene/polyethylene laminate (e.g., Steri-Drape™) or other fabric, paper, plastic, or similarly flexible and/or stretchable material. The material may or may not have a pre-cut aperture 62 therein for making a surgical incision.

In the embodiment illustrated in FIG. 3A, a plurality of electrode pairs $68^1/68^2$, $68^3/68^4$, $68^5/68^6$ are embedded in the material of the drape for applying the IFC therapy. The electrodes $68^1/68^2$, $68^3/68^4$, $68^5/68^6$ are connected to at least one power supply (14), as previously described. Once the sterile drape is in position on the patient in the sterile field, sterile wire ends can be connected to the electrodes via quick connection ports already mounted in the drape (60) or other customary means of connecting the wires thereto. The wires are of sufficient length to travel out of the surgical field so that a circulating nurse can connect the other end to the power supply.

Though the connection between the electrodes $68^1/68^2$, $68^3/68^4$, $68^5/68^6$ and power supply (14) can be a hardwire connection, it is often desirable to minimize the number of wires entering the sterile field. Therefore, in some embodiments, the electrodes include an antenna and are instead wirelessly connected to the power supply, as has been known in connection with the use of existing wireless TENS (Transcutaneous Electrical Nerve Stimulation) units.

The electrodes $68^1/68^2$, $68^3/68^4$, $68^5/68^6$ may comprise pads or other appropriate conductive material, some examples of which are described in further detail below. The electrodes can be of various sizes. The size of the electrode will affect the size of the target therapeutic area, and so generally speaking, the larger the electrodes $68^1/68^2$, $68^3/68^4$, $68^5/68^6$ can be while still reasonably fitting in the relevant type of dressing being employed, the better.

Regardless of whether the entire drape (60) is an adhesive drape, the portion of the drape that includes the electrodes $68^1/68^2$, $68^3/68^4$, $68^5/68^6$ has an adhesive backing. The drape and adhesive backings are flexible to allow any necessary motion, such as the repositioning of an extremity during the various stages of a surgical procedure, or the testing of the range of motion of that extremity. Accordingly, fenestrations or openings may be provided, and drapes such as a Steri-Drape™ or Coban™ self-adherent wrap may optimally be used as the sheet (60).

The electrode portions of the drape (60) include a conductivity backing that, in addition to the adhesive, is directly in contact with the skin. This can be a gel, such as the conductive gel commonly used with an ultrasound probe, or a moist pad, as is commonly used with EKG leads. The electrode portions are already provided with the gel or other conductive material, such that the drape (60) can be applied to the patient in a simple, sterile step during preparation for surgery.

Figure 3B:
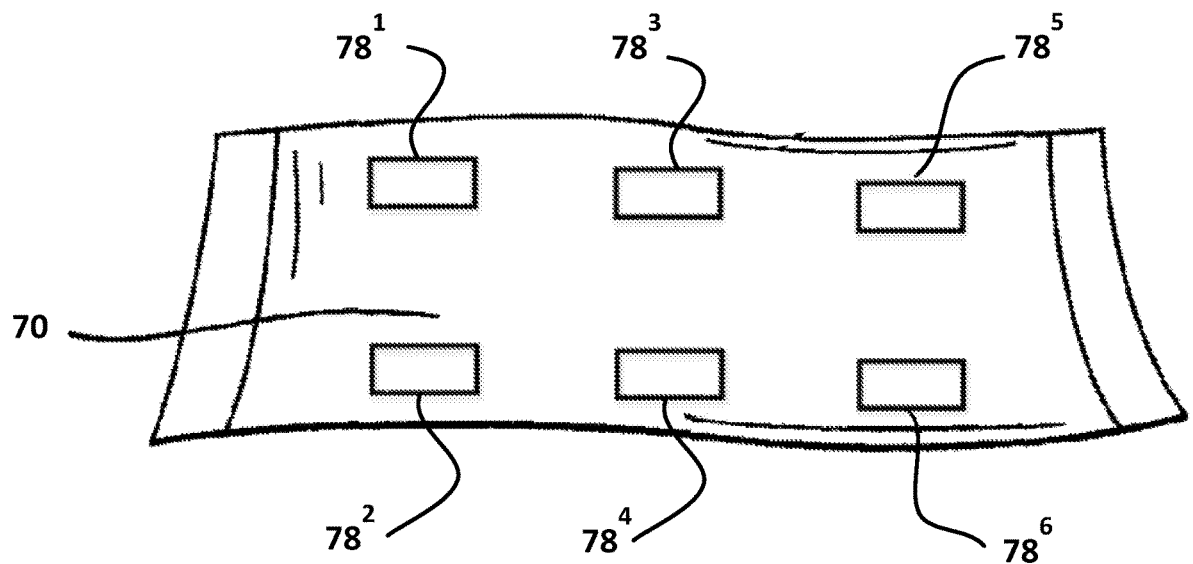

Another exemplary embodiment of a drape is illustrated in FIG. 3B. In these embodiments, a drape (70) includes a plurality of electrodes $78^1/78^2$, $78^3/78^4$, $78^5/78^6$ affixed to an outer surface of the drape. In some cases, the electrodes $78^1/78^2$, $78^3/78^4$, $78^5/78^6$ comprise a pad with an adhesive on one side, such that the electrodes $78^1/78^2$, $78^3/78^4$, $78^5/78^6$ can be affixed to the drape (70) after the drape has applied to the patient, and the wires to the power supply (14) then connected to the electrodes.

Figure 3C:
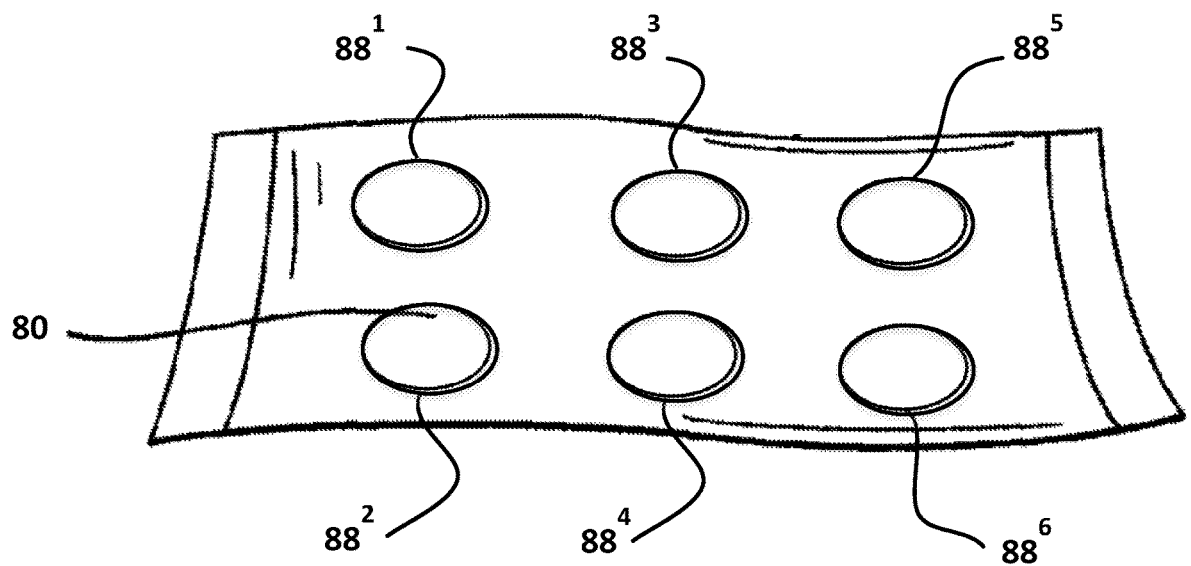

Another exemplary embodiment of a drape is illustrated in FIG. 3C. In these embodiments, a drape (80) includes a plurality of enclosed chambers therein. The chambers are filled with an electrically conductive fluid, such that they serve as electrodes $88^1/88^2$, $88^3/78^4$, $88^5/88^6$ for delivering the electrical stimulus.

Figure 3D:
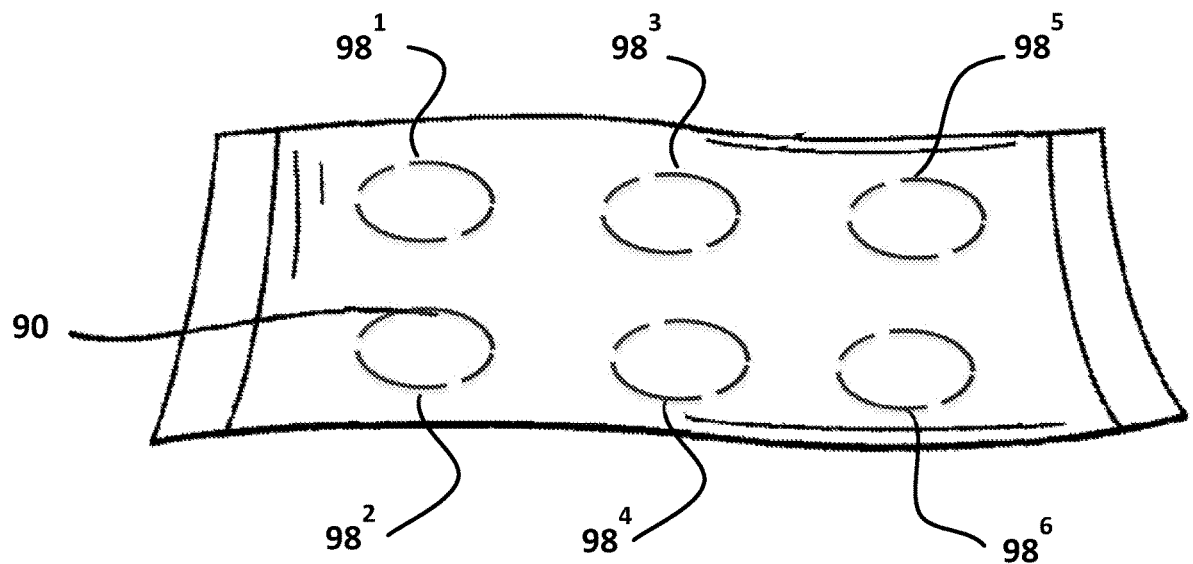

In another exemplary embodiment, the sheet (90) itself is fashioned from both electrically conductive and non-electrically conductive portions. As shown in FIG. 3D, in these embodiments, a plurality of segments of electrically conductive fabric serve as electrodes $98^1/98^2$, $98^3/98^4$, $98^5/98^6$ for delivering the electrical stimulus.

Referring now to FIG. 4A, a typical application of the surgical drape applying IFC therapy is shown. In this example, the invention is employed in connection with knee surgery.

A drape (100) is placed about the knee (110) of a patient, where an incision (112) is made and subsequently sewn together. The drape (100) has a series of electrode pairs $118^1/118^2$, $118^3/118^4$, which are connected via wires (120) to the power supply (114).

When bleeding occurs during the surgery, the surgeon or other medical practitioner causes the power supply (114) (e.g., by simply turning it on or by issuing a command via a controller, as described above) to supply power to the electrodes $118^1/118^2$, $118^3/118^4$. As a result, each electrode pair $118^1/118^2$ delivers electrical impulses at two different frequencies, giving rise to at least one beat impulse having an interference frequency.

The electrodes $118^1/118^2$ are located such that the therapeutic target area thereof is positioned to cause sympathetic nerve stimulation in order to cause vasoconstriction of blood vessels contributing to the undesirable bleeding. While activation of sympathetic nerves will typically cause vasodilatation relative to organs needed for a "fight or flight" response, sympathetic activation generally constricts blood vessels, thereby increasing vascular resistance and decreasing blood flow. This effect on the blood flow tends to be particularly prominent in relation to the skin, digestive tract, and skeletal muscle. Accordingly, upon receiving power from the power supply, the electrodes activate the sympathetic nerves to induce local constriction of the blood vessels in the targeted area, which operates to reduce, or stop, the flow of blood.

As mentioned previously, when activation of the sympathetic nerves it desirable, beat impulses having a frequency in the range of from 1-5 Hz may provide desirable stimulation properties.

In instances where it is desirable to achieve vasodilatation, the parasympathetic nerves can be targeted. For example, after repair of an incision/laceration and/or during recovery, there comes a time when active bleeding has stopped and, rather than needing to slow/stop blood flow, it may be desirable to induce vasodilatation to instead increase blood flow to the wound that is now trying to heal. At these times, the wound covering can be used to facilitate more rapid healing by targeting the parasympathetic nerves. As mentioned previously, when activation of the parasympathetic nerves is desirable, beat impulses having a frequency in the range of from 10-150 Hz may provide desirable stimulation properties.

As with electrode pair $118^2/118^2$, electrode pair $118^3/118^4$ is likewise positioned such the therapeutic target area thereof is positioned to cause the desired sympathetic or parasympathetic nerve stimulation in order to cause vasoconstriction of the blood vessels that are contributing to the undesirable bleeding. Any number of electrode pairs may be employed on the drape (100) in this manner.

Optionally, an ultrasound probe (116) or other targeting device/mechanism is used to image the blood flow as described above to help the medical practitioner assess whether particular electrodes at their particular locations are indeed having the intended effect at the relevant target area. Notably, in cases where the electrodes are affixed to the drape (100) via an adhesive, such as described in with reference to FIG. 3B, the electrodes can be removed and repositioned if the desired effect is not being achieved.

Figure 4B:
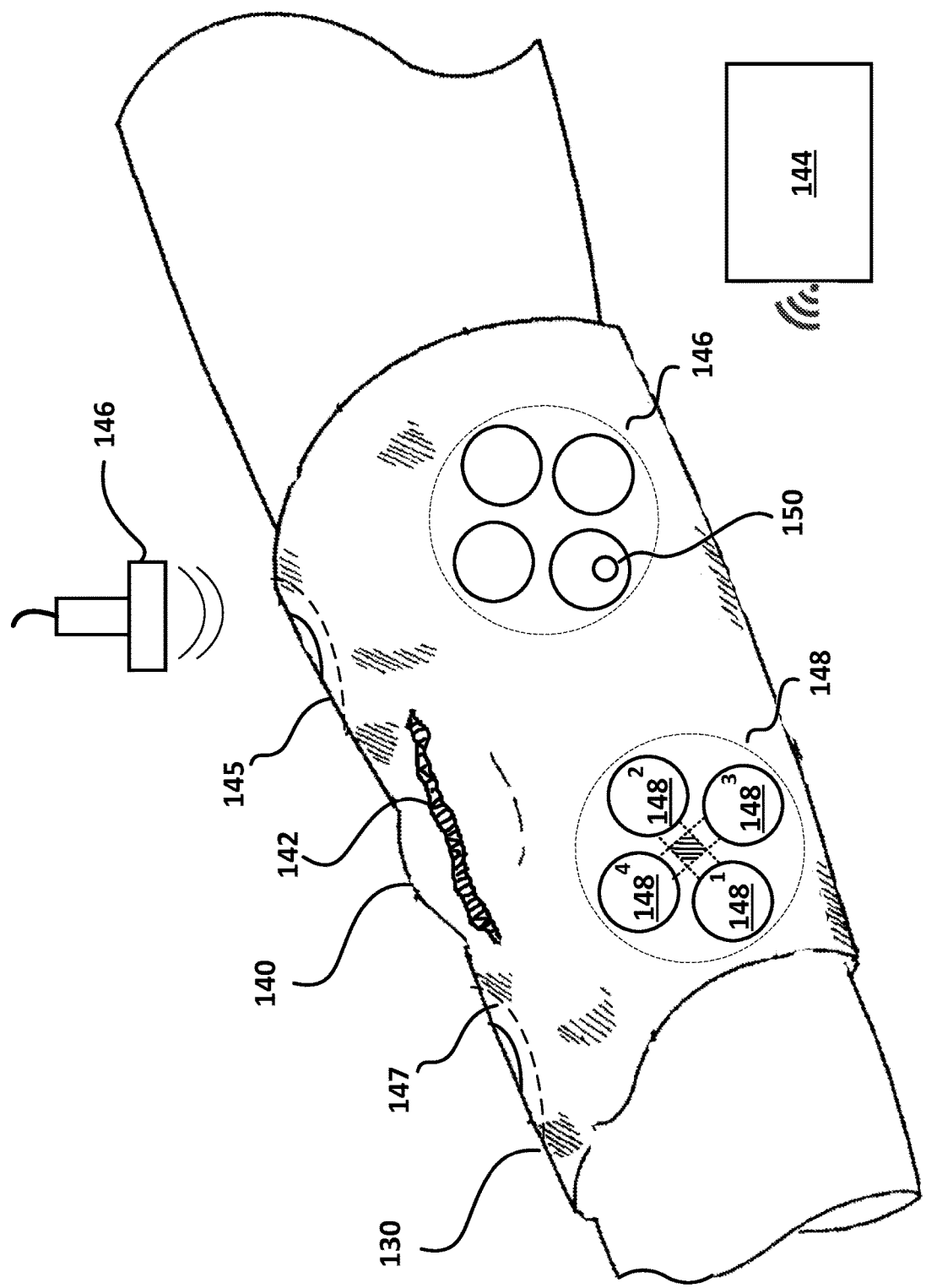
FIG. 4B is a partially perspective view of a wound covering illustrated in FIGS. 3A-D being used on a patient in a total knee arthroplasty procedure.

Referring now to FIG. 4B, an exemplary application of the surgical drape applying IFC therapy is shown. In this example, the invention is employed in connection with a total knee arthroplasty (TKA), or total knee replacement (TKR). Blood loss is a serious concern during these procedures, and allogeneic transfusions are commonly used to treat the acute blood loss and postoperative anemia that often occurs, but these transfusions are associated with the risks of allergic and immunologic reactions, and infection transmission. Hence, multiple blood-saving strategies have been employed to try to minimize blood loss, reduce transfusion rates, and decrease complications, for which the present invention is ideally suited.

In this instance, a self-adhesive drape (130), such as a Steri-Drape™ (130), is applied the patient's knee, and an incision (142) is cut through the drape (130). The drape may also have a pre-designed cut out area for the surgical incision. The cut out or incision window, or the incision made directly through the drape, does not affect the circuitry needed for surrounding electrodes to nonetheless continue to supply the IFC intersecting fields, which thus are arranged circumferentially around the cut out area. Similarly, because a TKA procedure involves the use of a large metal implant, interferential currents situated to go across the operative site may scatter as a result of interference from the metal. Accordingly, multiple sets of electrodes (145), (146), (147), (148) are positioned circumferentially around the operative site.

Additionally, electrodes (not shown) may be positioned in the portion of the drape (130) proximal to the operative field that would not directly cause vasoconstriction of vessels within the operative field, but rather, would intercept incoming arteries and smaller arterioles in the upper thigh, proximal to the area of the incision. As a result, bleeding is decreased, just as might be accomplished by a tourniquet when placed in the upper thigh area to cut off bleeding from the area distal thereto.

Each set of electrode pairs $148^1/148^2$, $148^3/148^4$ includes at least one antenna (150) for receiving power wirelessly from the power source. Each electrode may have its own antenna, or the electrodes in a localized set of electrodes $148^1$, $148^2$, $148^3$, $148^4$ may be wired together, such that only a single electrode $148^1$ needs to wirelessly receive power from the power supply (144), which it then communicates to the remaining electrodes $148^2$, $148^3$, $148^4$ in the localized set.

This system provides significant advantages over current methods of controlling surgical wound bleeding, such as the use of a Bovie® electrocoagulation device. This type of device employs a fine tip placed directly on a visualized bleeding artery or vein. The device is activated, usually with part of a hand control, and the blood vessel is electrocoagulated. As noted above, this damages small areas of surrounding tissue, and it can compromise skin-to-skin wound healing from one side of a wound to the other because of the thermal damage to small areas around where the device was used.

In addition, the electrocoagulation device requires a grounding plate placed on some other area of the body, usually the opposite lower extremity or an upper extremity, which is then connected to the electrocoagulation device because it is high voltage electric current. The grounding plate is outside the sterile field and outside the draping. This is then connected to the Bovie machine. There are issues with disconnecting that grounding plate and deactivating the machine before removing drapes and putting a dressing on a patient, and personnel have to be sure they do not cut the wires to and from the machine or the grounding plate, as there can be issues with electrical shock and fire hazard. Further, when the device is used directly on the wound, a small spark resulting from the electric impulse and the thermocoagulation that results also places the operating room at risk of fire if there is oxygen in the air.

The wireless supply of power described above also eliminates the disadvantage of an electrocoagulation device where the surgeon and assistants have to worry about where wires are located while moving around the operating table to be sure they do not step on, trip over, or pull out a wire connection.

In some embodiments, a drape (130) as already described can also be used in conjunction with a tourniquet. This can be a traditional tourniquet as already described, but with less tourniquet time required in view of effects of the IFC applied by the drape (130). A timer with an alarm may be provided, which alerts the surgeon that a certain interval for which the tourniquet has been applied has expired (e.g., 15 or 30 minutes, so that the surgeon can then deflate (or remove) the tourniquet to provide a recovery interval (e.g., 10 or 15 minutes) in order to avoid potential complications.

Figure 4C:
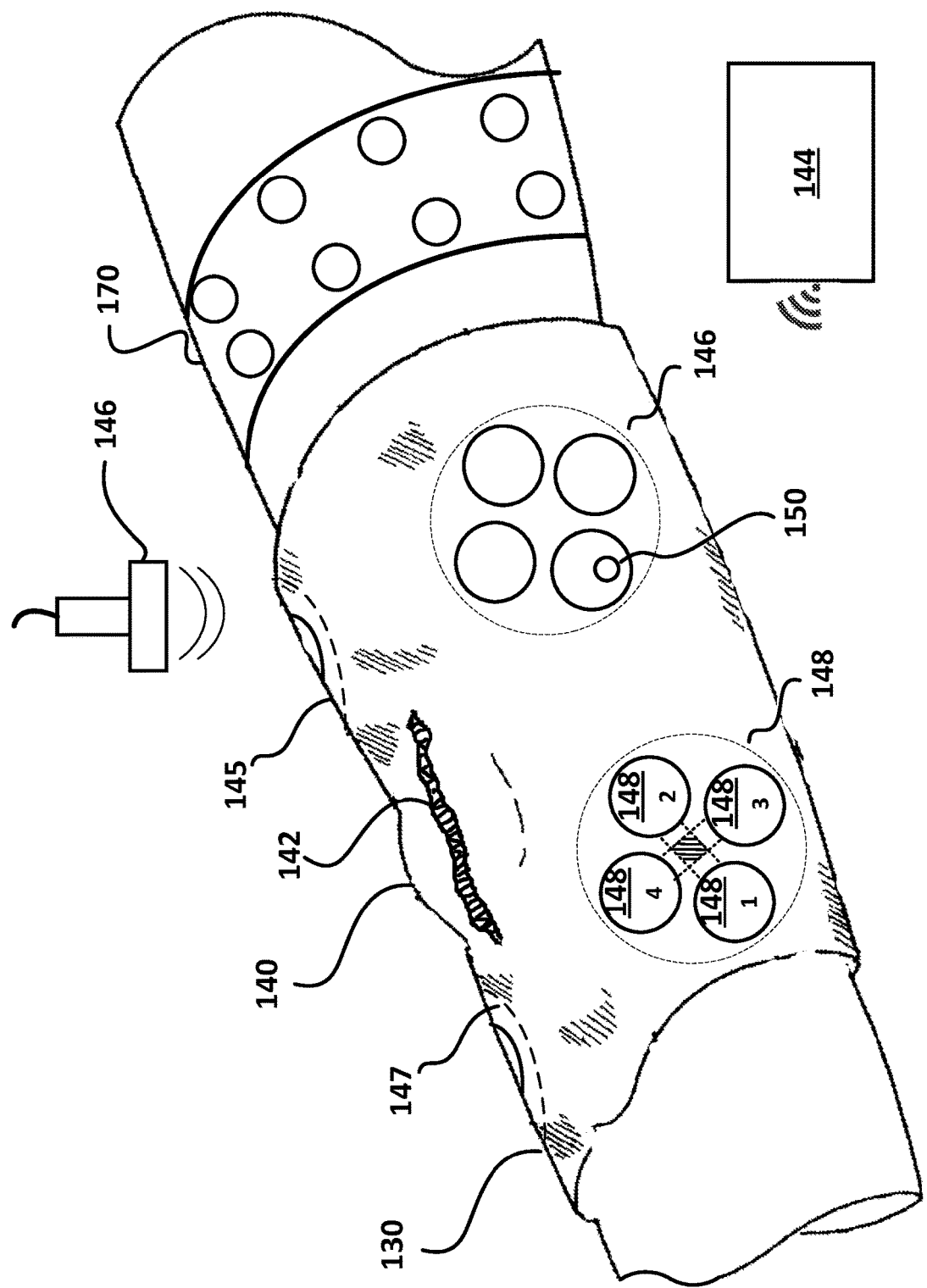
FIG. 4C is a partially perspective view of the wound covering illustrated in FIG. 4A in conjunction with a tourniquet.

Alternatively, as shown in FIG. 4C, the tourniquet can be a tourniquet (170) that employs a similar mechanism as the drape (130), using IFC rather than pneumatic pressure for control of extremity blood flow. The IFC tourniquet (170) is secured around the leg at a point proximal of the operative site, such that numerous pairs of electrodes $148^1$, $148^2$, $148^3$, $148^4$ are positioned around the circumference of the leg.

A user input of some form, such as on the controller (12) described above, may be provided for the tourniquet (170) and/or the drape (130) to allow a user to set the Hz level and program the device for either vasoconstriction or vasodilatation, depending on what is desired.

Although the invention has been described in connection with total knee arthroplasty, it can be used in connection with any surgical procedure in which intraoperative or post-operative control of bleeding is needed. For instance, sterile draping during endovascular or bypass surgery, and the treatment of peripheral vascular disease, are just two of many additional possible applications.

Figure 5A:
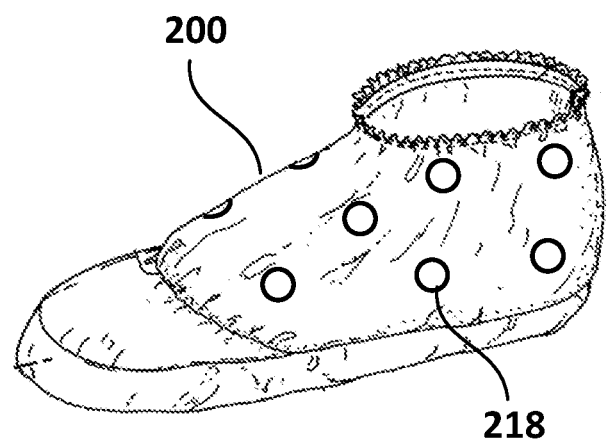
FIG. 5A is a perspective view of an exemplary wound covering used in the system illustrated in FIG. 1.

It should be noted that other types and configurations of coverings are contemplated. For example, the covering may take the form of a footwear covering, as shown in FIG. 5A. In these cases, the covering (200) is configured to have a shape corresponding to the shape of a foot, and has the electrodes (218) in the appropriate locations to provide their therapeutic effect. Such footwear coverings include surgical foot drapes, disposable or reusable booties, Rooke® boots, and any other offloading or vascular boots that may be required when treating wounded feet, such as when attending to peripheral vascular disease or after the debridement of diabetic foot ulcers. As noted above, a user input may be provided that allows a user to set the Hz level to program the foot covering for either vasoconstriction or vasodilatation, depending on what is desired.

Additionally, the invention is also applicable to other non-surgical applications, such as the dressing or treatment of a wound resulting from an accidental injury. In some embodiments, the flexible sheet is a medical dressing, such as a sterile pad or gauze. The medical dressing may be held in place over a wound with a separate bandage, or the dressing may be self-adhesive. As shown with respect to the self-adhesive dressing depicted in FIG. 5B, the sheet 230 includes an adhesive section 232 and a sterile pad 234 for dressing the wound. The adhesive section 232 includes a plurality of electrodes 236, which are electrically connected to wires 238, which are in turn connected to the power supply that supplies the interferential current or other electrical stimulus. Alternatively, the electrodes 236 may instead be provided on the sterile pad 234, and additionally, may instead be wirelessly connected to the power supply.

Figure 5C:
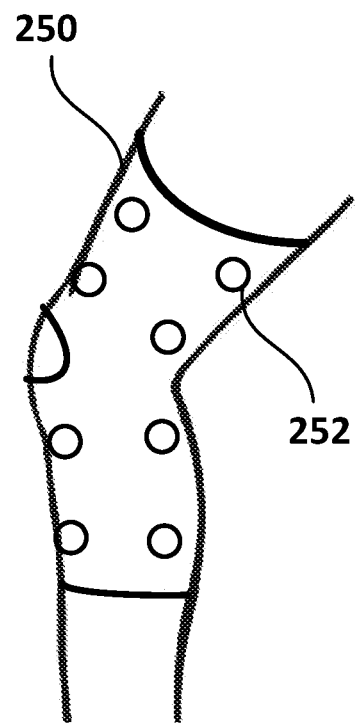
FIG. 5C is a perspective view of a neoprene brace used in the system illustrated in FIG. 1.
Figure 5B:
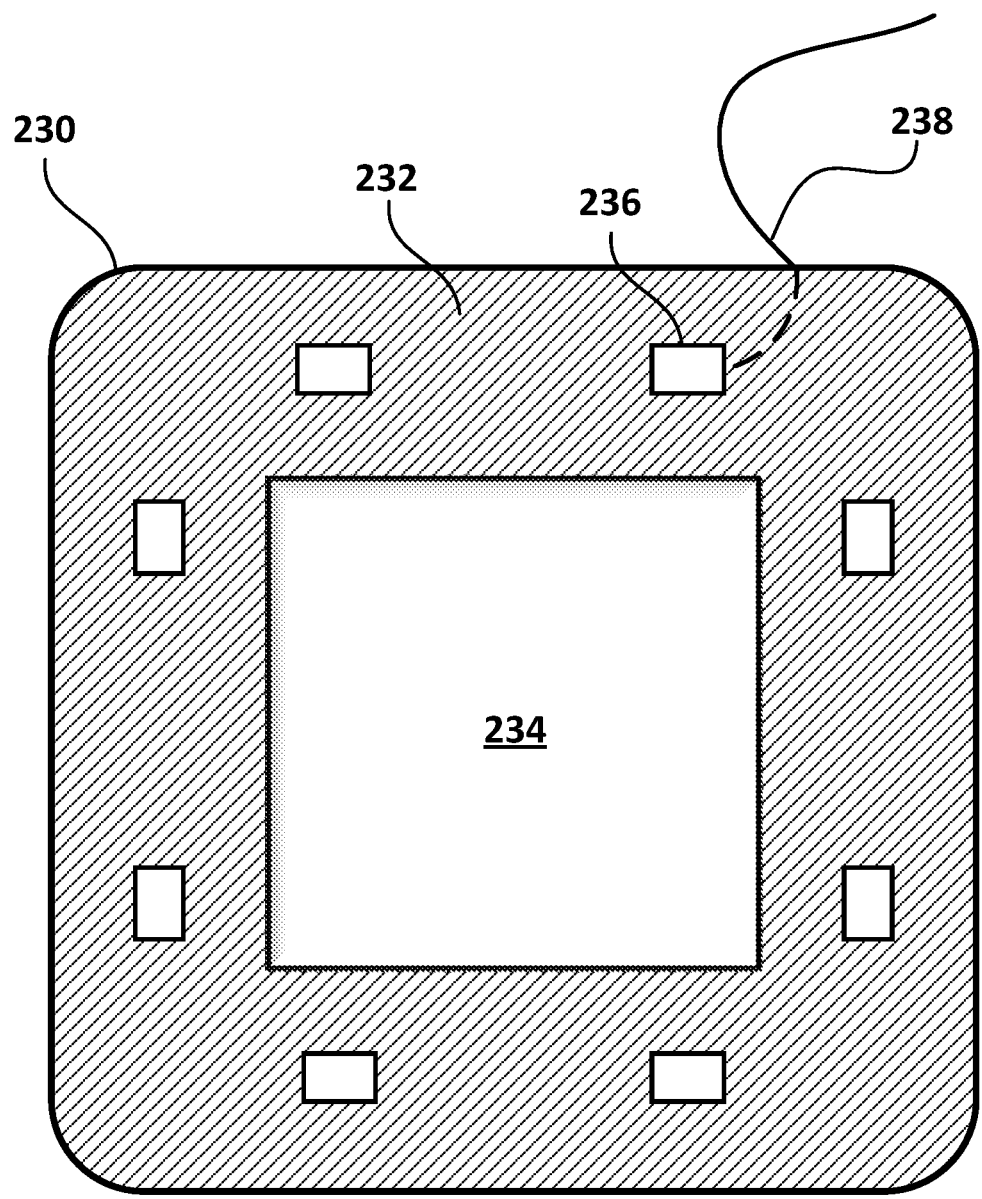
FIG. 5B of is an isometric view of another exemplary wound covering used in the system illustrated in FIG. 1.

In other embodiments, the sheet comprises a compression bandage, wrap or brace. For example, as illustrated in FIG. 5C, the above-described electrodes may be employed in a brace, such as a neoprene brace (250). This can be placed over the wound, with or without an ACE bandage, for compression in order to reduce swelling, as well as to reduce post-operative bleeding. The brace can be sized for the relevant patient and can be removed and put back on the wound for repetitive use over several days in the post-operative period, when nurses have to inspect the wound or do wound dressing changes. The sleeve allows range of motion, but has the electrodes (252) in the appropriate places to provide their therapeutic effect As noted above, a user input may be provided that allows a user to set the Hz level to program the brace for either vasoconstriction or vasodilatation, depending on what is desired.

An additional potential synergistic outcome of using the above-described wound covering employing electrical stimulation is a decrease in infection rates, which also has a further positive effective on wound healing.

Although the invention has been described with reference to particular arrangement of parts, features, and the like, these are not intended to exhaust all possible arrangements or features, and indeed many modifications and variations will be ascertainable by those of skill in the art.

The present invention is designed so that any electrical or mechanical types of deep penetration electrical stimulation that is non-invasive and external (i.e. transcutaneous) that are available but have not been incorporated into the description of the invention, or that become available as technology advances, are considered part of the invention and incorporated by modifying the electrical and mechanical parts and protocols associated with them to the achieve the aims of the present invention.

What is claimed is:

1. A medical wound covering for controlling blood flow, comprising:
    a flexible sheet for covering the anatomical site of a wound;
    wherein the flexible sheet includes a plurality of electrodes electrically connectible to a stimulation power supply that supplies current to the plurality of electrodes; and
    wherein the plurality of electrodes are configured to supply electrical impulses to the anatomical site of the wound in response to receiving the current from the stimulation power supply, the plurality of electrodes comprising a first pair of electrodes supplying a first electrical impulse at a first frequency, and a second pair of electrodes supplying a second electrical impulse at a second frequency different from the first frequency, the first and second pairs of electrodes positioned such that the first and second electrical impulses intersect at a target area; and
    wherein the stimulation power supply simultaneously supplies current to the first and second pairs of electrodes such that the first and second electrical impulses give rise to at least one beat impulse having a frequency lower than the first and second frequencies at the target area.

2. The medical wound covering of claim 1, wherein the flexible sheet comprises a surgical drape.

3. The medical wound covering of claim 2, wherein the surgical drape comprises an adhesive drape.

4. The medical wound covering of claim 1, wherein the flexible sheet comprises a medical dressing.

5. The medical wound covering of claim 1, wherein the flexible sheet comprises a bandage.

6. The medical wound covering of claim 1, wherein the stimulation power supply comprises an interferential therapy power supply, and wherein the plurality of electrodes comprises at least one pair of electrodes supplying electrical impulses at two different frequencies, the electrical impulses provided at two different frequencies giving rise to at least one beat impulse having an interference frequency.

7. The medical wound covering of claim 6, wherein the at least one beat impulse has a sympathetic nerve stimulation property to induce vasoconstriction of blood vessels.

8. The medical wound covering of claim 6, wherein the at least one beat impulse has a parasympathetic nerve stimulation property to induce vasodilatation of blood vessels.

9. The medical wound covering of claim 1, wherein the electrodes are embedded within the sheet.

10. The medical wound covering of claim 1, wherein each electrode includes an adhesive on a surface thereof, with which the electrode is affixed to an outer surface of the sheet.

11. The medical wound covering of claim 1, wherein:
    the sheet includes a plurality of enclosed chambers, each of the chambers having an electrically conductive liquid therein; and
    the electrodes comprise the electrically conductive liquid.

12. The medical wound covering of claim 1, wherein:
    the sheet includes a plurality of electrically conductive fabric segments of fabric; and
    the electrodes comprise the electrically conductive fabric segments.

13. The medical wound covering of claim 1, further comprising:
   a controller;
   a stimulation power supply in communication with the controller;
   a sensor providing sensor feedback to the controller, the sensor indicative of the state of blood flow at the anatomical site of the wound;
   wherein the controller causes the stimulation power supply to supply power to the plurality of electrodes based at least in part on the state of blood flow.

14. The medical wound covering of claim 13, wherein the sensor comprises a targeting or monitoring device.

15. The medical wound covering of claim 13, wherein the sensor comprises a Doppler ultrasound probe.

16. The medical wound covering of claim 1, wherein each electrode includes an electrical connector for connecting a wire to the stimulation power supply.

17. The medical wound covering of claim 1, wherein the stimulation power supply communicates wirelessly with the electrodes.

18. The medical wound covering of claim 1, wherein the flexible sheet is configured to have a shape corresponding to shape of a foot.

19. A method of controlling blood flow with a medical wound covering, the method comprising:
   covering an anatomical site of a wound with a flexible sheet having first and second pairs of electrodes;
   connecting the first and second pairs of electrodes to a stimulation power supply;
   supplying a first electrical impulse at a first frequency to a target area by supplying current to the first pair of electrodes from the stimulation power supply;
   supplying a second electrical impulse at a second frequency different from the first frequency to the target area by supplying current to the second pair of electrodes such that the second electrical impulse intersects with the first electrical impulse at the target area, the first and second electrical impulses giving rise to at least one beat impulse having a frequency lower than the first and second frequencies at the target area.

20. The method of claim 19, wherein:
   the stimulation power supply comprises an interferential therapy power supply.

21. The method claim 19, wherein the flexible sheet comprises a surgical drape.

22. The method of claim 21, wherein the surgical drape comprises an adhesive drape.

23. The method of claim 19, wherein the at least one beat impulse has a sympathetic nerve stimulation property to induce vasoconstriction of blood vessels.

24. The method of claim 19, wherein the at least one beat impulse has a parasympathetic nerve stimulation property to induce vasodilatation of blood vessels.

* * * * *